United States Patent [19]

Parnell

[11] Patent Number: 5,248,501
[45] Date of Patent: * Sep. 28, 1993

[54] DRUG DELIVERY SYSTEMS CONTAINING ERIODICTYON FLUID EXTRACT AS AN EXCIPIENT, AND METHODS AND COMPOSITIONS ASSOCIATED THEREWITH

[75] Inventor: Francis W. Parnell, Ross, Calif.

[73] Assignee: Parnell Pharmaceuticals, Larkspur, Calif.

[*] Notice: The portion of the term of this patent subsequent to May 14, 2008 has been disclaimed.

[21] Appl. No.: 667,547

[22] Filed: Mar. 11, 1991

Related U.S. Application Data

[63] Continuation-in-part of Ser. No. 608,336, Nov. 2, 1990, Pat. No. 5,128,132, which is a continuation-in-part of Ser. No. 499,952, Mar. 26, 1990, Pat. No. 5,015,474, which is a continuation-in-part of Ser. No. 275,124, Nov. 22, 1988, Pat. No. 4,938,963.

[51] Int. Cl.$^5$ .................. A61K 35/78; A61L 9/70
[52] U.S. Cl. .................. 424/195.1; 424/448; 424/449; 514/783
[58] Field of Search .......... 424/195.1, 448, 449; 514/783

[56] References Cited

U.S. PATENT DOCUMENTS

| | | | |
|---|---|---|---|
| 164,674 | 6/1875 | Cooper | 424/195.1 |
| 174,442 | 3/1876 | Rohrer | 424/195.1 |
| 404,422 | 6/1889 | Maxwell et al. | 424/195.1 |
| 3,965,908 | 6/1976 | Posthuma et al. | 128/303 R |
| 4,128,631 | 12/1978 | Lundmark et al. | 424/70 |
| 4,184,974 | 1/1980 | Van Leuvin | 252/106 |
| 4,205,073 | 5/1980 | Sherlock et al. | |
| 4,232,003 | 11/1980 | Posthuma et al. | 424/81 |
| 4,267,168 | 5/1981 | Van Leuvin | 424/75 |
| 4,347,237 | 8/1982 | Evenstad et al. | 424/78 |
| 4,438,100 | 3/1984 | Balsev et al. | 424/104 |
| 4,617,293 | 10/1986 | Wahlig et al. | 514/41 |
| 4,661,475 | 4/1987 | Bayerlein et al. | |
| 4,906,169 | 3/1990 | Chien | |
| 4,906,476 | 3/1990 | Radhakrishnan | 424/450 |
| 4,912,117 | 3/1990 | Carr | 514/317 |
| 4,933,169 | 6/1990 | Shanbrom | 424/46 |
| 4,938,963 | 7/1990 | Parnell | |
| 4,956,171 | 9/1990 | Chang | |
| 4,978,531 | 12/1990 | Yamazari | 424/448 |
| 4,983,378 | 1/1991 | Parnell | |
| 5,015,474 | 5/1991 | Parnell | 424/195.1 |

OTHER PUBLICATIONS

The National Formulary, published 1 Jan. 1985 by the U.S. Pharmacopeial Convention, (Maryland), 5 pages total.
N. Coon, *Using Plants for Healing*, Hearthside Press, 1963, at p. 122.
N. C. Coon, *The Dictionary of Useful Plants*, Emmaus, Pa.: Odale Press, 1974.
M. Grieve, *A Modern Herbal*, vol. 22, New York: Hafner Publishing Col., 1969, at p. 865.
B. C. Harris, *The Compleat Herbal*, Barre, Mass. Barre Publishers, 1972 at p. 197.
P. Huson, *Mastering Herbalish: A Practical Guide*, New York: Stein and Day, 1974, at p. 32.
A. R. Hutchens, *Indian Herbalogy of North America*, Ontario: Merco, 1975, at pp. 317-318.
W. H. Lewis et al., *Medical Botany: Plants Affecting Man's Health*, New York: John Wiley & Sons, 1977, at p. 301.
M. Moore, *Los Remedios de la Gente: A Compilation of Traditional New Mexican Herbal Medicines and Their Use*, 1977.

(List continued on next page.)

*Primary Examiner*—Michael G. Wityshyn
*Assistant Examiner*—Ralph Gitomer
*Attorney, Agent, or Firm*—Reed & Robins

[57] ABSTRACT

Methods, compositions and systems are provided for delivering a drug to the skin or mucosa. The invention involves the use of eriodictyon fluid extract as an excipient in compositions and systems for administering drugs topically, transdermally or transmucosally. The invention also relates to methods of using eriodictyon fluid extract to reduce skin or mucosal irritation and as a moisturizer.

31 Claims, No Drawings

OTHER PUBLICATIONS

D. G. Spoerke, *Herbal Medications*, Santa Barbara, Calif.: Woodbridge Press, 1980, at p. 183.

G. E. Trease et al., *Pharmacognosy*, London: Cassell & Colber, 1978, at p. 463.

V. E. Tyler et al., *Pharmacognosy*, Philadelphia: Lee & Febiger, 1981, at p. 148.

V. J. Vogel, *American Indian Medicine*, The University of Oklahoma Press 1970 at pp. 83, 399–400.

U.S. patent application Ser. No. 07/499,952, filed 26 Mar. 1990, entitled "Composition For Imparting Moisture To A Substrate" (inventor Parnell).

U.S. patent application Ser. No. 07/608,336, filed 20 Nov. 1990, entitled "Compositions And Methods For Treating Internal Mucous Membranes" (inventor Parnell).

DRUG DELIVERY SYSTEMS CONTAINING ERIODICTYON FLUID EXTRACT AS AN EXCIPIENT, AND METHODS AND COMPOSITIONS ASSOCIATED THEREWITH

This application is a continuation-in-part of U.S. Ser. No. 07/608,336, filed 2 Nov. 1990, now U.S. Pat. No. 5,128,132, which is a continuation-in-part of U.S. Ser. No. 07/499,952, filed 26 Mar. 1990, now U.S. Pat. No. 5,015,474, which is a continuation-in-part of U.S. Ser. No. 275,124, filed 22 Nov. 1988, now U.S. Pat. No. 4,938,963.

TECHNICAL FIELD

This invention relates generally to methods, compositions and systems for delivering a drug to the skin or mucosa. More particularly, the invention relates to the use of eriodictyon fluid extract as an excipient in compositions and systems that are designed to administer a drug topically, transdermally or transmucosally.

BACKGROUND

It is well known to administer drugs to or through the skin or mucosa. Such a mode of delivery provides many advantages; primarily, topical, transdermal or transmucosal delivery are generally comfortable, convenient and noninvasive ways of administering drugs. The variable rates of absorption and metabolism encountered with oral treatment are avoided, and other inconveniences—gastrointestinal irritation and the like—are eliminated as well.

A number of problems have been encountered with the aforementioned modes of drug administration, however. The skin or mucosa can become irritated or sensitized by a particular drug, adhesive or skin permeation enhancer. Pain and itching may result and be serious enough that the patient may discontinue use of the drug. In addition, the skin may become dry or flaky upon continued administration of a particular pharmaceutical composition. If such problems persist and are severe enough in a large fraction of patients, a particular drug may simply be designated as unsuitable for administration to the skin or mucosa, even though therapeutically effective blood levels may have been achieved by administering the drug in this way.

The present invention is premised on the completely unexpected discovery that the oil extracted from the Yerba Santa plant (Eriodictyon californicum; Eriodictyon glutinosum; also known as "eriodictyon fluid extract"; "consumptive's weed"; "bear's weed"; "mountain balm"; and "gum plant") is extremely effective as an excipient in compositions for application to the skin or mucosa, and minimizes or completely eliminates the irritation, sensitization and dryness which often accompanies topical, transdermal or transmucosal drug delivery. The novel excipient also makes possible the administration of a wider range of drugs than previously believed possible, i.e., drugs which caused a significant degree of the aforementioned problems in a relatively large fraction of patients.

The Yerba Santa plant is an evergreen shrub indigenous to the hills and mountains of California and northern Mexico, and was long used by Indians for a number of purposes. See, e.g., A. R. Hutchens, *Indian Herbalogy of North America*, Ontario: Merco, 1975, at pp. 317-318. A number of references to the Yerba Santa plant teach its use as an expectorant (e.g., N. Coon, *The Dictionary of Useful Plants*, Emmaus, Pa.: Rodale Press, 1974)), in treating colds, sore throats, catarrh, stomach aches, vomiting and diarrhea (see A. R. Hutchens, supra), in treating hemorrhoids (D. G. Spoerke, *Herbal Medications*, Santa Barbara, Calif.: Woodbridge Press, 1980, at p. 183), in treating diseases of the lung (*Los Remedios de la Gente: A Compilation of Traditional New Mexican Herbal Medicines and Their Use*, compiled by M. Moore, 1977), and in masking the taste of quinine and other bitter medications (Spoerke, supra; see also G. E. Trease et al., *Pharmacognosy*, London: Cassell & Colber, 1978, at p. 463)). However, the present discovery that eriodictyon fluid extract is extremely effective in ameliorating the problems associated with delivery of certain drugs to the skin or mucosa is believed to be novel and completely unsuggested by the art.

Other Background Art

References related to the Yerba Santa plant, in addition to the Coon, Hutchens, Moore, Spoerke, and Trease et al. references cited in the preceding section, include V. J. Vogel, *American Indian Medicine*, The University of Oklahoma Press, 1970, at pp. 83, 399-400; W. H. Lewis et al., *Medical Botany: Plants Affecting Man's Health*, New York: John Wiley & Sons, 1977, at p. 301; P. Huson, *Mastering Herbalism: A Practical Guide*, New York: Stein and Day, 1974, at p. 32; B. C. Harris, *The Compleat Herbal*, Barre, Mass.; Barre Publishers, 1972, at p. 197; N. Coon, *Using Plants for Healing*, Hearthside Press, 1963, at p. 122; M. Grieve, *A Modern Herbal*, vol. 22, New York: Hafner publishing Co., 1969, at p. 865; and V. E. Tyler et al., *Pharmacognosy*, Philadelphia: Lee & Febiger, 1981, at p. 148.

SUMMARY OF THE INVENTION

Accordingly, it is a primary object of the present invention to address the above-identified need in the art, and to provide methods, compositions and drug delivery systems for topical, transdermal or transmucosal drug administration, which involve the use of eriodictyon fluid extract as an excipient.

In one aspect of the invention, a system is provided for delivering a drug to the skin or mucosa, the system comprising:

(a) a source of the drug to be administered;

(b) a source of an excipient composition comprising eriodictyon fluid extract; and (c) a means for maintaining the system in drug and excipient composition transmitting relationship to the skin or mucosa.

In a preferred embodiment, this aspect involves a laminated structure wherein the drug and the excipient composition are present in a drug reservoir which is a polymeric adhesive matrix (or wherein the drug and the excipient composition are present in two or more such matrices) adapted to adhere to the skin, and wherein the reservoir is laminated to a backing material that serves as the upper surface of the device during use and is made of a material that is substantially impermeable to the drug and to the excipient composition.

In another aspect, the invention encompasses pharmaceutical compositions containing a drug and the eriodictyon-based excipient. These compositions may be simply a mixture of drug and eriodictyon fluid extract, wherein the eriodictyon fluid extract serves as an excipient, or they may be mixtures of drug, eriodictyon-based excipient, and one or more vehicles, carriers, diluents, permeation enhancers, or the like. The composition may be in the form of a solution, suspension, ointment, gel, cream, etc..

In still another aspect, the invention is directed to a method of facilitating adherence of an agent to the skin or mucosa, the method involving applying the agent to the skin or mucosa in conjunction with an excipient composition containing eriodictyon fluid extract. This aspect of the invention is based on the discovery that eriodictyon fluid extract is useful as a bioadhesive, i.e., a species which will increase adhesion of a device (e.g., a transdermal drug delivery device) or chemical species (such as a drug in an ointment, gel, solution or suspension) to the skin or mucosal tissue. In related aspects, other methods of using compositions containing eriodictyon fluid extract are provided. One method involves reducing skin or mucosal irritation, while another method involves moisturizing the skin or mucosal tissue. Both of these methods involve application of a composition containing eriodictyon fluid extract to the affected skin or tissue site.

DETAILED DESCRIPTION OF THE INVENTION

Before describing the present compositions, systems and methods of the invention in detail, it is to be understood that this invention is not limited to the particular drugs, laminate materials, or dosage regimens described herein as such may, of course, vary. It is also to be understood that the terminology used herein is for the purpose of describing particular embodiments only, and is not intended to be limiting since the scope of the present invention will be limited only by the appended claims.

It must be noted that, as used in this specification and the appended claims, the singular forms "a," "an" and "the" include plural referents unless the context clearly dictates otherwise. Thus, for example, reference to a laminated structure containing "a drug" includes a mixture of two or more drugs, reference to "an adhesive" includes reference to one or more of such adhesives, and reference to "a solvent" includes reference to a mixture of two or more solvents.

Other definitions of words and phrases used throughout this specification and the appended claims are as follows:

The term "drug" as used herein is intended to mean a compound or composition of matter which, when administered to an organism (human or animal) induces a desired pharmacologic and/or physiologic effect by local and/or systemic action. In general, the terms include the therapeutic or prophylactic agents in all major therapeutic/prophylactic areas of medicine. Examples of drugs useful in conjunction with the present invention include: anti-infectives such as antibiotics and antiviral agents; analgesics and analgesic combinations; anorexics; antihelminthics; antiarthritics; antiasthmatic agents; anticholinergic agents; anticonvulsants; antidepressants; antidiabetic agents; antidiarrheals; antihistamines; anti-inflammatory agents, antimigraine preparations; anti-motion sickness drugs; antinauseants; antineoplastics; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; steroids; hypnotics; immunosuppressives; muscle relaxants; parasympatholytics; psychostimulants; sedatives; tranquilizers; and agents for alleviating drug withdrawal symptoms.

For purposes of the aforementioned definition, "drugs" as used herein also include locally administered topical medicaments such as antibacterial agents, antifungals, antimicrobials, cutaneous growth enhancers, antipsoriatics, anti-acne medicaments, sunscreens and the like.

The term "effective amount" as used herein intends that quantity of material which, when used or administered to a patient as indicated, is sufficient to provide the desired or intended beneficial effect. For example, when used in the present context, the term "effective amount" of eriodictyon fluid extract in the moisturizing method is that which is sufficient to provide a desired degree of moisturizing, and will of course vary with the individual and the degree of dryness. An "effective amount" of eriodictyon fluid extract to alleviate chemically induced irritation, e.g., irritation resulting from topical, transdermal or transmucosal administration of a drug, is an amount which is sufficient to provide a desired degree of relief. Again, the "effective amount" in this latter case will vary with the individual, the degree of irritation, and possibly with the particular type of chemical or drug, if any, which is inducing the irritation.

By "eriodictyon fluid extract" or "Yerba Santa fluid extract" as used herein is meant the fluid which may be extracted from dried Yerba Santa leaves. One exemplary method for obtaining this Yerba Santa fluid extract is set forth in *Remington's Pharmaceutical Sciences*, 17th Ed., 1985, at pp. 1286 and 1516, which is incorporated herein by reference to disclose such an extraction method. As described in detail in the aforementioned reference, the dried Yerba Santa plant is preferably processed in alcohol and water, followed by straining, pressing and clarification by, for example, decantation or filtration.

By "transdermal" (or "percutaneous") drug delivery, applicant is using the term in its conventional sense, i.e., to indicate delivery of a drug by passage through the skin and into the blood stream. By "transmucosal" drug delivery applicant intends delivery of a drug by passage of a drug through the mucosal tissue into the blood stream. "Topical" drug delivery is used to mean local administration of a topical drug as in, for example, the treatment of various skin disorders. These terms will sometimes be used interchangeably herein, i.e., aspects of the invention which are described in the context of "transdermal" drug delivery, unless otherwise specified, can apply to transmucosal or topical delivery as well. That is, the compositions, systems, and methods of the invention, unless explicitly stated otherwise, should be presumed to be equally applicable with any one of these three modes of drug delivery.

"Carriers" or "vehicles" as used herein refer to carrier materials suitable for transdermal, transmucosal or topical drug administration, and include any such materials known in the art, e.g., any liquid, gel, solvent, liquid diluent, solubilizer, or the like, which is nontoxic and which does not interact with other components of the particular composition or system in a deleterious manner. Examples of suitable carriers for use herein include water, mineral oil, silicone, nontoxic organic solvents, petroleum jelly, and a variety of other materials. The particular carrier or vehicle selected will depend on the particular system used, the desired rate of drug administration, as well as on the particular drug and its solubility in various solvents.

By "substantially impermeable" as used herein to describe the backing layer is meant that an effective amount of the selected drug and the excipient composition containing eriodictyon fluid extract will be contained within the drug delivery system or device without loss of any substantial amount through the backing layer.

The drug delivery systems of the invention contain a source of drug, a source of a pharmaceutically acceptable excipient composition containing eriodictyon fluid extract, and a means for maintaining the system in drug and eriodictyon fluid transmitting relationship to the skin or mucosa, i.e., such that both the selected drug and the eriodictyon fluid are applied to the desired area.

In one embodiment, the drug and excipient composition are contained within a laminated structure that serves as a drug delivery device to be affixed to a predetermined area of unbroken skin or mucosal tissue. In such a structure, the drug and the excipient composition are contained in a layer, or "reservoir", of a pharmaceutically acceptable polymeric adhesive composition. The laminated structure may contain a single reservoir, or it may contain multiple reservoirs. Suitable materials for the reservoir layer include polyethylenes, polysiloxanes, polyisobutylenes, polyacrylates, polyurethanes, or the like. The particular polymeric adhesive selected will depend on the particular drug, vehicle, carrier, enhancer, etc. that are used, i.e., the adhesive must be compatible with all components of the drug-containing composition.

In such a structure, the upper surface of the reservoir (or, if a plurality of reservoirs are present, the uppermost surface thereof) is laminated to an upper backing layer which functions as the primary structural element of the device and provides the device with much of its flexibility. The material selected for the backing material should be selected so that it is substantially impermeable to the drug and to the eriodictyon fluid extract, thus preventing loss of either component via transmission through the upper surface of the device. The backing layer may be occlusive or nonocclusive, depending on whether it is desired that the skin become hydrated during drug delivery. The backing is preferably made of a sheet or film of a preferably flexible elastomeric material. Examples of polymers that are suitable for the backing layer include polyethylene, polypropylene, polyesters, and the like.

During storage, the laminated structure includes a release liner. Immediately prior to use, this layer is removed from the device to expose the basal surface of the drug reservoir which serves as the means for adhering the system to the skin or mucosa. The release liner will normally be made from a drug/excipient impermeable material.

Such devices may be fabricated using conventional techniques, known in the art, for example by casting a fluid admixture of adhesive, drug, and excipient onto the backing layer, followed by lamination of the release liner. Similarly, the adhesive mixture may be cast onto the release liner, followed by lamination of the backing layer. Alternatively, the drug reservoir may be prepared in the absence of drug or excipient, and then loaded by "soaking" in a drug/excipient mixture.

The drug/excipient composition actually contained within the device and delivered therefrom to the skin or mucosa may take a number of forms. For liquid assays, the drug may be delivered "neat," i.e., in the absence of additional liquid. Alternatively, the drug may be dissolved, dispersed or suspended in a suitable pharmaceutically acceptable solvent or gel. The excipient composition contains eriodictyon fluid extract as its active ingredient, and may or may not contain any additional components. Typically, the excipient composition will be eriodictyon fluid extract itself. In some cases, however, other carriers or vehicles as described above may be incorporated into the excipient composition as well. Still other components can be incorporated into the excipient composition, including preservatives, stabilizers, surfactants, coloring agents, and the like. The drug/excipient composition in the reservoir will typically contain on the order of 0.1 to 20.0 wt. %, more preferably about 0.1 to 10.0 wt. %, most preferably about 0.5 to 5.0 wt. %, eriodictyon fluid extract (i.e., relative to the total drug/excipient composition), with the amount of drug dependent on a variety of factors, including the desired rate of delivery, the desired dosage, the disease to be treated, the nature and activity of the drug, the desired effect, possible adverse reactions, the ability and speed of the agent selected to reach its intended target, and other factors within the particular knowledge of the patient and the physician.

In other embodiments of the invention, the drug/excipient composition just described is administered in the form of a solution, suspension, ointment, gel or cream, rather than in a laminated drug delivery device. In these embodiments, the desired amount of drug contained within the composition will depend on a variety of factors, as outlined above, while the amount of eriodictyon fluid extract in the composition will typically be on the order of 0.1 to 20.0 wt. %, more preferably 0.1 to 10.0 wt. %, and most preferably 0.5 to 5 wt. %, i.e., relative to the total drug/eriodictyon composition. These solutions, suspensions, ointments, gels and creams will contain a pharmaceutically acceptable carrier liquid and/or solvent, ointment, gel or cream base, as well known in the art, plus the drug and the excipient composition containing eriodictyon fluid extract.

As noted above, a wide variety of drugs can be used in conjunction with the compositions and devices of the present invention. Preferred drugs within the classes identified earlier herein include but are not limited to the following: analgesics such as aspirin, ibuprofen and acetaminophen; antibiotics such as sulfacetamide, clindamycin and erythromycin; anticholinergic agents such as scopolamine; antidiabetic agents such as insulin; antifungal agents such as nystatin; antihistamines such as diphenhydramine; antinauseants such as meclozine; antineoplastic agents such as fluorouracil; antipsychotics such as prochlorperazine; decongestants such as oxymetazoline, phenylephrine and ephedrine; steroids such as hydrocortisone, progesterone, and estrogens; and compositions for treating drug withdrawal containing, e.g., a CNS stimulant such as caffeine and a serotonin antagonist such as dihydroergotamine or a salt thereof (such compositions are described in applicant's co-pending, commonly assigned U.S. patent application Ser. No. 07/500,034, filed 27 Mar. 1990, now U.S. Pat. No. 5,051,426, and entitled "METHOD AND COMPOSITIONS FOR EFFECTING WITHDRAWAL FROM DRUG DEPENDENCY", the disclosure of which is incorporated by reference herein).

Since the inherent permeability of skin or mucosal tissue to some drugs (e.g., steroids) is too low to permit therapeutic levels of drugs to pass through a reasonably sized area of unbroken skin, it is necessary to coadminister a skin permeation enhancer with such drugs. Accordingly, in such cases, the enhancer will be present in the drug/excipient formulation, either in the drug reservoir of a laminated drug delivery system or in a solution, ointment, gel or cream.

The pharmaceutical compositions and systems of the invention can be used in different ways to accomplish somewhat different purposes. The drug delivery device described above is preferred for administering drugs transdermally or transmucosally, and the eriodictyon fluid present in the excipient composition is useful in significantly reducing local irritation or sensitization that so frequently occurs with this type of drug delivery. For topical administration, use of a solution, ointment, cream or gel is preferred. Again, the eriodictyon fluid significantly reduces the likelihood of local skin or mucosal problems arising from drug administration, and further, facilitates adherence of the drug to the skin or mucosal tissue. The eriodictyon fluid extract is also useful in moisturizing the skin, as it can prevent or eliminate dryness for significant periods of time.

EXAMPLES

The following examples are put forth so as to provide those of ordinary skill in the art with a complete disclosure and description of how to make and use the compositions and systems of the present invention, and are not intended to limit the scope of what the inventor regards as his invention. Unless otherwise indicated, parts are parts by weight, temperature is in degrees Centigrade, and pressure is at or near atmospheric.

EXAMPLE 1

(a.) A transdermal patch for administering a composition containing dihydroergotamine mesylate and caffeine may be prepared as follows. A laminate of a polyacrylate drug reservoir layer and a polyethylene backing layer is soaked in an aqueous solution containing 2.5 wt. % eriodictyon fluid extract, 4 mg/ml dihydroergotamine ("DHE") mesylate, and 8 mg/ml caffeine citrate until absorption of the fluidic composition ceases. A layer of a polyester release liner is then applied to the basal surface of the drug reservoir to protect the patch prior to use. To administer the composition to alleviate drug withdrawal symptoms in a drug-addicted individual (suffering from addiction to, e.g., amphetamines, cocaine, or nicotine), the release liner is removed and the patch is applied to a selected area of the individual's skin or mucosal tissue.

(b.) A transdermal patch for administering a composition containing dihydroergotamine mesylate and caffeine may alternatively be prepared as follows. Precursors to the desired polyacrylate, e.g., acrylate monomers and a crosslinking agent, are admixed with the above-mentioned aqueous solution and the mixture is stirred to uniformity. The drug/adhesive composition is then cast onto a polyester release liner, followed by lamination of the polyethylene backing layer to form the upper surface of the device.

EXAMPLE 2

(a.) A transdermal patch for administering a composition containing acetaminophen may be prepared as follows. A laminate of a polyacrylate drug reservoir layer and a polyethylene backing layer is soaked in an aqueous solution containing 2.5 wt. % eriodictyon fluid extract and 30 mg/ml acetaminophen until absorption of the fluidic composition ceases. A layer of a polyester release liner is then applied to the basal surface of the drug reservoir to protect the patch prior to use. To administer the composition to effect analgesia in a patient in need of such treatment, the release liner is removed and the patch is applied to a selected area of the individual's skin or mucosal tissue.

(b.) A transdermal patch for administering acetaminophen may also be made according to the method outlined in Example 1(b), above.

EXAMPLE 3

A solution of oxymetazoline for nasal administration was prepared as summarized in the following table:

| Components | Quantity |
| --- | --- |
| Water | 90.0 wt. % |
| Eriodictyon Fluid Extract | 2.5 wt. % |
| pH Buffer | 1.5 wt. % |
| Sodium Chloride | 5.0 wt. % |
| Oxymetazoline | 1.0 wt. % |

The above composition is useful as a nasal spray. The composition may further include other active components as desired. The sodium chloride is added in an amount to adjust to the saline composition of normal nasal mucosal tissues, as is the pH of the composition.

EXAMPLE 4

A solution of amantadine for nasal administration was prepared as summarized in the following table:

| Components | Quantity |
| --- | --- |
| Water | 90.0 wt. % |
| Eriodictyon Fluid Extract | 2.5 wt. % |
| pH Buffer | 1.5 wt. % |
| Sodium Chloride | 5.0 wt. % |
| Amantadine | 1.0 wt. % |

The solution is buffered as described in the preceding example, and, optimally, is administered as a nasal spray.

EXAMPLE 5

A solution of diphenhydramine hydrochloride was prepared as summarized in the following table:

| Components | Quantity |
| --- | --- |
| Water | 90.0 wt. % |
| Eriodictyon Fluid Extract | 2.5 wt. % |
| pH Buffer | 1.5 wt. % |
| Sodium Chloride | 5.0 wt. % |
| Diphenhydramine Hydrochloride | 1.0 wt. % |

As in the preceding examples, the solution is optimally administered as a oral solution irrigator. A decongestant may be incorporated as an additional active ingredient.

EXAMPLE 6

An ointment of fluorouracil for topical administration was prepared as summarized in the following table:

| Components | Quantity |
| --- | --- |
| Excipient (ointment base) | 95.75 wt. % |
| Eriodictyon Fluid Extract | 1.5 wt. % |

-continued

| Components | Quantity |
| --- | --- |
| Preservative | 0.25 wt. % |
| Fluorouracil | 2.5 wt. % |

EXAMPLE 7

An ointment of nystatin for topical or transmucosal administration was prepared as summarized in the following table:

| Components | Quantity |
| --- | --- |
| Excipient (ointment base) | 94.25 wt. % |
| Eriodictyon Fluid Extract | 1.5 wt. % |
| Preservative | 0.25 wt. % |
| Nystatin | 4.0 wt. % |

On to two teaspoons of the above ointment is applied to the targeted skin area.

EXAMPLE 8

A clindamycin-based antibacterial gel was prepared as summarized in the following table:

| Components | Quantity |
| --- | --- |
| Excipient (gel base) | 97.25 wt. % |
| Eriodictyon Fluid Extract | 1.5 wt. % |
| Preservative | 0.25 wt. % |
| Clindamycin | 1.0 wt. % |

One to two teaspoons of the above gel may be applied to the skin or mucosal area in need of antibacterial treatment.

EXAMPLE 9

A hydrocortisone cream for topical administration was prepared as summarized in the following table:

| Components | Quantity |
| --- | --- |
| Excipient (cream base) | 97.25 wt. % |
| Eriodictyon Fluid Extract | 1.5 wt. % |
| Preservative | 0.25 wt. % |
| Hydrocortisone | 1.0 wt. % |

One to two teaspoons of the above cream may be applied to the skin or mucosal area in need of treatment.

EXAMPLE 10

As estrogen cream for topical administration was prepared as summarized in the following table:

| Components | Quantity |
| --- | --- |
| Excipient (cream base) | 97.25 wt. % |
| Eriodictyon Fluid Extract | 1.5 wt. % |
| Preservative | 0.25 wt. % |
| Estrogen | 1.0 wt. % |

One to two teaspoons of the above cream may be applied to the skin or mucosal area in need of treatment.

EXAMPLE 11

A sunscreen formulation was prepared as summarized in the following table:

| Components | Quantity |
| --- | --- |
| Excipient (cream base) | 92.25 wt. % |
| Eriodictyon Fluid Extract | 2.5 wt. % |
| Preservative | 0.25 wt. % |
| p-Amino Benzoic Acid | 5.0 wt. % |

The cream may be applied topically, as desired, to reduce to the risk of sunburn upon exposure of the skin to the sun.

The above formulations may be used in the treatment of a wide variety of medical conditions in humans in animals. They may be used to treat conditions such as drug addiction (Example 1), to relieve pain (Example 2), as an adrenergic agent (Example 3), to effect sinus drainage (Example 5), to provide topical anti-neoplastic action (Example 6), as an antifungal composition (Example 7), as an antibacterial composition (Example 8), as an anti-inflammatory and anti-itching composition (Example 9), as well as to treat various types of skin aberrations (Example 10), or as a sunscreen (Example 11).

A primary advantage of each of these formulations is to provide more uniform, variably increased absorption of a specific drug across mucous membranes and/or skin that, with traditional excipients, are obtained only minimally or not at all.

I claim:

1. A transdermal drug delivery device for delivering a drug to the skin or mucosa of a patient, comprising:
a reservoir containing the drug and a pharmaceutically acceptable excipient composition comprising eriodictyon fluid extract, wherein the reservoir comprises a pharmaceutically acceptable polymeric adhesive matrix having an upper surface and a basal surface adapted to adhere to the skin or mucosa, and wherein the drug is selected such that it can be delivered to the patient through the skin or mucosa of the patient in a pharmaceutically effective amount; and
a backing layer laminated to the reservoir, which serves as the upper surface of the device and is substantially impermeable to the drug and the excipient composition.

2. The device of claim 1, further including a release liner layer laminated to the basal surface of the reservoir, and adapted to be removed from the device prior to use to expose the basal surface of the polymeric adhesive matrix.

3. A transdermal drug delivery device for delivering a drug to skin or mucosa of a patient, comprising:
a reservoir containing a drug and an excipient, wherein the drug is selected such that it can be delivered to the patient through the skin or mucosa of the patient in a pharmaceutically effective amount, and wherein the excipient comprises eriodictyon fluid extract, the drug and excipient being maintained in the reservoir in a transmitting relationship to the skin;
a backing layer defining an upper surface of the device, the backing layer being substantially impermeable to the pharmaceutically active drug and the excipient; and
an adhesive positioned on the device in a manner allowing the device to be adhered to the skin or mucosa.

4. The device of claim 3, wherein approximately 0.1 to 20.0 wt. % eriodictyon fluid extract is present in the carrier liquid.

5. The device of claim 4, wherein approximately 0.1 to 10.0 wt. % eriodictyon fluid extract is present in the carrier liquid.

6. The device of claim 5, wherein approximately 0.5 to 5.0 wt. % eriodictyon fluid extract is present in the carrier liquid.

7. The device of claim 3, wherein the reservoir is comprised of the drug, excipient and adhesive intermixed to form a polymeric adhesive matrix.

8. The device of claim 3, wherein the drug and excipient are each present in separate polymeric adhesive matrices which are laminated to each other.

9. The device of claim 3, further comprising:
a pharmaceutically acceptable carrier liquid dispersed throughout the polymeric adhesive matrix.

10. A pharmaceutical composition for delivering a drug to the skin or mucosa of a patient, comprising:
(a) a drug which is selected from the group consisting of fluorouracil, nystatin, clindamycin, hydrocortisone, and estrogen;
(b) a pharmaceutically acceptable excipient composition comprising eriodictyon fluid extract, wherein the eriodictyon fluid represents about 0.1 wt. % to about 20.0 wt. % of the pharmaceutical composition; and
(c) a pharmaceutically acceptable base selected from the group consisting an ointment base, a gel base and a cream base, such that the pharmaceutical composition exists as an ointment, gel or cream, respectively.

11. The pharmaceutical composition of claim 10, wherein the eriodictyon fluid extract represents about 0.1 wt. % to 10.0 wt. % of the pharmaceutical composition.

12. The pharmaceutical composition of claim 11, wherein the eriodictyon fluid extract represents about 0.5 wt. % to 5.0 wt. % of the pharmaceutical composition.

13. The pharmaceutical composition of claim 10, wherein the base is an ointment base, such that the pharmaceutical composition exists as an ointment.

14. The pharmaceutical composition of claim 10, wherein the base is a gel base, such that the pharmaceutical composition exists as a gel.

15. The pharmaceutical composition of claim 10, wherein the base is a cream base, such that the pharmaceutical composition exists as a cream.

16. The pharmaceutical composition of claim 10, wherein the drug is fluorouracil.

17. The pharmaceutical composition of claim 10, wherein the drug is nystatin.

18. The pharmaceutical composition of claim 10, wherein the drug is clindamycin.

19. The pharmaceutical composition of claim 10, wherein the drug is hydrocortisone.

20. The pharmaceutical composition of claim 10, wherein the drug is estrogen.

21. A method for moisturizing the skin or mucosa, comprising applying to the skin or mucosa a moisturizing composition comprising an effective moisturizing amount of eriodictyon fluid extract in a base selected from the group consisting of an ointment base, a gel base, a cream base, and a carrier liquid, such that the moisturizing composition exists as an ointment, gel, cream, or solution, respectively.

22. A method for reducing chemically induced irritation of the skin or mucosal tissue, comprising applying a pharmaceutical composition containing an irritation-reducing effective amount of eriodictyon fluid extract to the affected area, wherein the pharmaceutical composition additionally includes a base selected from the group consisting of an ointment base, a gel base, a cream base, and a carrier liquid, such that the pharmaceutical composition exists as an ointment, gel, cream, or solution, respectively.

23. The method of claim 22, wherein the eriodictyon fluid extract represents approximately 0.1 wt. % to 2.0 wt. % of the pharmaceutical composition.

24. The method of claim 23, wherein the eriodictyon fluid extract represents about 0.1 wt. % to 10.0 wt. % of the pharmaceutical composition.

25. The method of claim 24, wherein the eriodictyon fluid extract represents about 0.5 wt. % to 5.0 wt. % of the pharmaceutical composition.

26. The method of claim 22, wherein the base is an ointment base, such that the pharmaceutical composition exists in the form of an ointment.

27. The method of claim 22, wherein the base is a cream base, such that the pharmaceutical composition exists in the form of a cream.

28. The method of claim 22, wherein the base is a gel base, such that the pharmaceutical composition exists in the form of a gel.

29. A pharmaceutical composition for nasal administration of a drug selected from the group consisting of oxymetazoline and amantidine, comprising a saline solution or suspension of an amount of the drug sufficient to provide the desired therapeutic effect, approximately 0.1 wt. % to 20.0 wt. % eriodictyon fluid extract, and a pH buffer effective to adjust the pH of the composition to that of normal nasal mucosal tissues.

30. The pharmaceutical composition of claim 29, containing approximately 0.1 wt. % to 10.0 wt. % eriodictyon fluid extract.

31. The pharmaceutical composition of claim 30, containing approximately 0.1 wt. % to 5.0 wt. % eriodictyon fluid extract.

* * * * *